US005720959A

United States Patent [19]
Holder et al.

[11] Patent Number: 5,720,959
[45] Date of Patent: Feb. 24, 1998

[54] MALARIA VACCINE

[75] Inventors: Anthony A. Holder, Biggin Hill; Michael J. Blackman, Kettering; Jonathan A. Chappel, Fakenham, all of United Kingdom

[73] Assignee: Medical Research Council, England

[21] Appl. No.: 290,919

[22] PCT Filed: Feb. 22, 1993

[86] PCT No.: PCT/GB93/00367

§ 371 Date: Oct. 4, 1994

§ 102(e) Date: Oct. 4, 1994

[87] PCT Pub. No.: WO93/17107

PCT Pub. Date: Sep. 2, 1993

[30] Foreign Application Priority Data

Feb. 22, 1992 [GB] United Kingdom ............... 9203821

[51] Int. Cl.$^6$ .................. A61K 39/015; C07K 14/445
[52] U.S. Cl. .................. 424/272.1; 424/185.1; 424/268.1; 435/69.3; 435/320.1; 530/300; 530/350; 530/395; 536/23.5
[58] Field of Search .................. 530/300, 350, 530/395, 403; 424/185.1, 268.1, 272.1; 435/69.3, 360.1, 252.1; 536/23.4, 23.5

[56] References Cited

U.S. PATENT DOCUMENTS 4,837,016  6/1989  Holder et al. ............... 424/88

OTHER PUBLICATIONS

Blackman et al: "Proteolytic processing of the Plasmodium falciparum merozoite surface protein–1 produces a membrane–bound fragment containing two epidermal growth factor–like domains", Molecular and Biochemical Parasitology, 49 (1991) 29–34.

Holder et al: "Processing of the precursor to the major merozoite surface antigens of Plasmodium falciparum", Parasitology, vol. 94, No. 2, Apr. 1987, pp. 199–208.

Blackman, et al: "A single fragment of a malaria merozoite surface protein remains on the parasite during red cell invasion and is the target of invasion–inhibiting antibodies", J. Exp. Med., vol. 172, Jul. 1990, pp. 379–382.

Kaslow et al: "A vaccine candidate from the sexual stage of human malaria that containes EGF–like domains", Nature, vol. 333, May 1988, pp. 74–76.

Burns et al: "A protective monoclonal antibody recognizes an epitope in the carboxyl–terminal cysteine–rich domain in the precursor of the major merozoite surface antigen of the rodent malarial parasite, Plasmodium yoelii", Journal of Immunology, vol. 143, No. 8, Oct. 1989, pp. 2670–2676.

Smith, et al "Single step purification of polypeptides expressed in Escherichia coli as fusions with glutathione S–transferase", Gene, vol. 67, No. 1, Jul. 1988, pp. 31–40.

Chappel, et al: "Monoclonal antibodies specific for merozoite surface protein 1 in Plasmodium–falciparum recognize epidermal growth factor–like motifs", Abstract Gen Meet. Am Soc. Microbiol, vol. 92, No. 0, 1992, p. 61.

Primary Examiner—Thomas M. Cunningham
Attorney, Agent, or Firm—Cushman Darby & Cushman IP Group of Pillsbury Madison & Sutro

[57] ABSTRACT

Disclosed are novel polypeptides comprising the sequences substantially as shown in FIGS. 1 and 2, in isolation from sequences naturally occuring adjacent thereto in the merozoide suface protein MSP1. Also disclosed are vectors comprising nucleotide sequences encoding said polypeptides, host cells comprising said vectors and a vaccine comprising one or both novel polypeptides.

21 Claims, 6 Drawing Sheets

MSP1EGF1$_A$

MSP1EGF1$_B$

MSP1EGF2_A

MSP1EGF2_B

SEQUENCE LISTING ( 1 ) GENERAL INFORMATION:

( i i i ) NUMBER OF SEQUENCES: 19

( 2 ) INFORMATION FOR SEQ ID NO:1:

( i ) SEQUENCE CHARACTERISTICS:
        ( A ) LENGTH: 48 amino acids
        ( B ) TYPE: amino acid
        ( C ) STRANDEDNESS: single
        ( D ) TOPOLOGY: linear     ( i i ) MOLECULE TYPE: protein     ( i x ) FEATURE:
        ( A ) NAME/KEY: Modified-site
        ( B ) LOCATION: 1
        ( D ) OTHER INFORMATION: /label=X
            / note="X =M and N, or N"

( x i ) SEQUENCE DESCRIPTION: SEQ ID NO:1:

```
Xaa  Ile  Ser  Gln  His  Gln  Cys  Val  Lys  Lys  Gln  Cys  Pro  Gln  Asn  Ser
1                   5                        10                      15

Gly  Cys  Phe  Arg  His  Leu  Asp  Glu  Arg  Glu  Glu  Cys  Lys  Cys  Leu  Leu
                20                      25                      30

Asn  Tyr  Lys  Gln  Glu  Gly  Asp  Lys  Cys  Val  Glu  Asn  Pro  Asn  Pro  Thr
           35                      40                      45
```

( 2 ) INFORMATION FOR SEQ ID NO:2:

( i ) SEQUENCE CHARACTERISTICS:
        ( A ) LENGTH: 48 amino acids
        ( B ) TYPE: amino acid
        ( C ) STRANDEDNESS: single
        ( D ) TOPOLOGY: linear     ( i i ) MOLECULE TYPE: protein     ( i x ) FEATURE:
        ( A ) NAME/KEY: Modified-site
        ( B ) LOCATION: 1
        ( D ) OTHER INFORMATION: /label=X
            / note="X =M and N, or N"

( x i ) SEQUENCE DESCRIPTION: SEQ ID NO:2:

```
Xaa  Ile  Ser  Gln  His  Gln  Cys  Val  Lys  Lys  Gln  Cys  Pro  Glu  Asn  Ser
1                   5                        10                      15

Gly  Cys  Phe  Arg  His  Leu  Asp  Glu  Arg  Glu  Glu  Cys  Lys  Cys  Leu  Leu
                20                      25                      30

Asn  Tyr  Lys  Gln  Glu  Gly  Asp  Lys  Cys  Val  Glu  Asn  Pro  Asn  Pro  Thr
           35                      40                      45
```

( 2 ) INFORMATION FOR SEQ ID NO:3:

( i ) SEQUENCE CHARACTERISTICS:
        ( A ) LENGTH: 53 amino acids
        ( B ) TYPE: amino acid
        ( C ) STRANDEDNESS: single
        ( D ) TOPOLOGY: linear     ( i i ) MOLECULE TYPE: protein     ( i x ) FEATURE:
        ( A ) NAME/KEY: Modified-site
        ( B ) LOCATION: 1
        ( D ) OTHER INFORMATION: /label=X
            / note="X =M and N, or N"

( x i ) SEQUENCE DESCRIPTION: SEQ ID NO:3:

```
Xaa  Pro  Asn  Pro  Thr  Cys  Asn  Glu  Asn  Asn  Gly  Gly  Cys  Asp  Ala  Asp
1                   5                        10                      15

Ala  Lys  Cys  Thr  Glu  Glu  Asp  Ser  Gly  Ser  Asn  Gly  Lys  Lys  Ile  Thr
                20                      25                      30
```

```
Cys Glu Cys Thr Lys Pro Asp Ser Tyr Pro Leu Phe Asp Gly Ile Phe
        35                  40                  45

Cys Ser Ser Ser Asn
        50
```

(2) INFORMATION FOR SEQ ID NO:4:

(i) SEQUENCE CHARACTERISTICS:
        (A) LENGTH: 53 amino acids
        (B) TYPE: amino acid
        (C) STRANDEDNESS: single
        (D) TOPOLOGY: linear     (ii) MOLECULE TYPE: protein     (ix) FEATURE:
        (A) NAME/KEY: Modified-site
        (B) LOCATION: 1
        (D) OTHER INFORMATION: /label=X
        / note="X =M and N, or N"

(xi) SEQUENCE DESCRIPTION: SEQ ID NO:4:

```
Xaa Pro Asn Pro Thr Cys Asn Glu Asn Asn Gly Gly Cys Asp Ala Asp
1                5                  10                  15

Ala Thr Cys Thr Glu Glu Asp Ser Gly Ser Ser Arg Lys Lys Ile Thr
        20                  25                  30

Cys Glu Cys Thr Lys Pro Asp Ser Tyr Pro Leu Phe Asp Gly Ile Phe
        35                  40                  45

Cys Ser Ser Ser Asn
        50
```

(2) INFORMATION FOR SEQ ID NO:5:

(i) SEQUENCE CHARACTERISTICS:
        (A) LENGTH: 42 base pairs
        (B) TYPE: nucleic acid
        (C) STRANDEDNESS: both
        (D) TOPOLOGY: linear     (ii) MOLECULE TYPE: cDNA     (xi) SEQUENCE DESCRIPTION: SEQ ID NO:5:

TAAGAGCTCG GGATCCAGAT GAACATTTCA CAACACCAAT GC        42

(2) INFORMATION FOR SEQ ID NO:6:

(i) SEQUENCE CHARACTERISTICS:
        (A) LENGTH: 35 base pairs
        (B) TYPE: nucleic acid
        (C) STRANDEDNESS: both
        (D) TOPOLOGY: linear     (ii) MOLECULE TYPE: cDNA     (xi) SEQUENCE DESCRIPTION: SEQ ID NO:6:

TCCGAGCTCA GATCTTAAGT AGGATTTGGA TTTTC        35

(2) INFORMATION FOR SEQ ID NO:7:

(i) SEQUENCE CHARACTERISTICS:
        (A) LENGTH: 42 base pairs
        (B) TYPE: nucleic acid
        (C) STRANDEDNESS: both
        (D) TOPOLOGY: linear     (ii) MOLECULE TYPE: cDNA     (xi) SEQUENCE DESCRIPTION: SEQ ID NO:7:

```
TAAGAGCTCG GGATCCAGAT GAATCCAAAT CCTACTTGTA AC                    42
```

( 2 ) INFORMATION FOR SEQ ID NO:8:

( i ) SEQUENCE CHARACTERISTICS:
        ( A ) LENGTH: 35 base pairs
        ( B ) TYPE: nucleic acid
        ( C ) STRANDEDNESS: both
        ( D ) TOPOLOGY: linear     ( i i ) MOLECULE TYPE: cDNA     ( x i ) SEQUENCE DESCRIPTION: SEQ ID NO:8:

```
TCCGAGCTCA GATCTTAGTT AGAGGAACTG CAGAA                            35
```

( 2 ) INFORMATION FOR SEQ ID NO:9:

( i ) SEQUENCE CHARACTERISTICS:
        ( A ) LENGTH: 42 base pairs
        ( B ) TYPE: nucleic acid
        ( C ) STRANDEDNESS: both
        ( D ) TOPOLOGY: linear     ( i i ) MOLECULE TYPE: cDNA     ( x i ) SEQUENCE DESCRIPTION: SEQ ID NO:9:

```
TAAGAGCTCG GGATCCACAT GGATGGTATG GATTTATTAG GT                    42
```

( 2 ) INFORMATION FOR SEQ ID NO:10:

( i ) SEQUENCE CHARACTERISTICS:
        ( A ) LENGTH: 35 base pairs
        ( B ) TYPE: nucleic acid
        ( C ) STRANDEDNESS: double
        ( D ) TOPOLOGY: linear     ( i i ) MOLECULE TYPE: cDNA     ( x i ) SEQUENCE DESCRIPTION: SEQ ID NO:10:

```
TCCGAGCTCA GATCTTAGCT GGAAGAACTA CAGAA                            35
```

( 2 ) INFORMATION FOR SEQ ID NO:11:

( i ) SEQUENCE CHARACTERISTICS:
        ( A ) LENGTH: 106 amino acids
        ( B ) TYPE: amino acid
        ( C ) STRANDEDNESS: single
        ( D ) TOPOLOGY: linear     ( i i ) MOLECULE TYPE: protein     ( x i ) SEQUENCE DESCRIPTION: SEQ ID NO:11:

```
Met Asp Gly Met Asp Leu Leu Gly Val Asp Pro Lys His Val Cys Val
1               5                   10                  15
Asp Thr Arg Asp Ile Pro Lys Asn Ala Gly Cys Phe Arg Asp Asp Asn
            20                  25                  30
Gly Thr Glu Glu Trp Arg Cys Leu Leu Gly Tyr Lys Lys Gly Glu Gly
        35                  40                  45
Asn Thr Cys Val Glu Asn Asn Asn Pro Thr Cys Asp Ile Asn Asn Gly
    50                  55                  60
Gly Cys Asp Pro Thr Ala Ser Cys Gln Asn Ala Glu Ser Thr Glu Asn
65                  70                  75                  80
Ser Lys Lys Ile Ile Cys Thr Cys Lys Glu Pro Thr Pro Asn Ala Tyr
                    85                  90                  95
Tyr Glu Gly Val Phe Cys Ser Ser Ser
                100                 105
```

( 2 ) INFORMATION FOR SEQ ID NO:12:

( i ) SEQUENCE CHARACTERISTICS:
        ( A ) LENGTH: 48 amino acids
        ( B ) TYPE: amino acid
        ( C ) STRANDEDNESS: single
        ( D ) TOPOLOGY: linear     ( i i ) MOLECULE TYPE: peptide     ( x i ) SEQUENCE DESCRIPTION: SEQ ID NO:12:

```
Asn Ile Ser Gln His Gln Cys Val Lys Lys Gln Cys Pro Gln Asn Ser
1               5                   10                  15

Gly Cys Phe Arg His Leu Asp Glu Arg Glu Glu Cys Lys Cys Leu Leu
            20                  25                  30

Asn Tyr Lys Gln Glu Gly Asp Lys Cys Val Glu Asn Pro Asn Pro Thr
            35                  40                  45
```

( 2 ) INFORMATION FOR SEQ ID NO:13:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear     ( i i ) MOLECULE TYPE: peptide     ( x i ) SEQUENCE DESCRIPTION: SEQ ID NO:13:

```
Glu Leu Gly Ile Gln Met Asn Ile Ser Gln His Gln Cys
1               5                   10
```

( 2 ) INFORMATION FOR SEQ ID NO:14:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear     ( i i ) MOLECULE TYPE: peptide     ( x i ) SEQUENCE DESCRIPTION: SEQ ID NO:14:

```
Glu Asn Pro Asn Pro Thr
1               5
```

( 2 ) INFORMATION FOR SEQ ID NO:15:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear     ( i i ) MOLECULE TYPE: peptide     ( x i ) SEQUENCE DESCRIPTION: SEQ ID NO:15:

```
Glu Leu Gly Ile Gln Met Asn Pro Asn Pro Thr Cys Asn
1               5                   10
```

( 2 ) INFORMATION FOR SEQ ID NO:16:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear (i i) MOLECULE TYPE: peptide (x i) SEQUENCE DESCRIPTION: SEQ ID NO:16:

Phe Cys Ser Ser Ser Asn
1               5

(2) INFORMATION FOR SEQ ID NO:17:

(i) SEQUENCE CHARACTERISTICS:
       (A) LENGTH: 13 amino acids
       (B) TYPE: amino acid
       (C) STRANDEDNESS: single
       (D) TOPOLOGY: linear (i i) MOLECULE TYPE: peptide (x i) SEQUENCE DESCRIPTION: SEQ ID NO:17:

Glu Leu Gly Ile His Met Asp Gly Met Asp Leu Leu Gly
1               5                   10

(2) INFORMATION FOR SEQ ID NO:18:

(i) SEQUENCE CHARACTERISTICS:
       (A) LENGTH: 6 amino acids
       (B) TYPE: amino acid
       (C) STRANDEDNESS: single
       (D) TOPOLOGY: linear (i i) MOLECULE TYPE: peptide (x i) SEQUENCE DESCRIPTION: SEQ ID NO:18:

Phe Cys Ser Ser Ser Ser
1               5

(2) INFORMATION FOR SEQ ID NO:19:

(i) SEQUENCE CHARACTERISTICS:
       (A) LENGTH: 35 base pairs
       (B) TYPE: nucleic acid
       (C) STRANDEDNESS: single
       (D) TOPOLOGY: linear (i i) MOLECULE TYPE: cDNA (x i) SEQUENCE DESCRIPTION: SEQ ID NO:19:

TTCTGTAGTT CTTCCAGCTA AGATCTGAGC TCGGA            3 5

MALARIA VACCINE

This application is a 371 of PCT/GB93/00367, filed Feb. 22, 1993.

FIELD OF THE INVENTION

The present invention relates to the identification of antigenic portions of malaria proteins, their expression in host cells, particularly bacteria, and their potential use as a vaccine.

BACKGROUND OF THE INVENTION

Malaria is caused by protozoal parasites of the genus Plasmodium. There are four species that infect man, *P. falciparum P, vivax, P. malariae* and *P. ovale*. Of these *P. falciparum* is largely responsible for acute and often fatal malaria, but there is significant morbidity associated with each malaria infection and a large proportion of the world's population is at risk from the disease. It has been estimated that malaria is a public health problem in areas where 40% of the world's population live and the disease has severe social and economic consequences for these communities. There has been a recent resurgence of the disease due to the abandonment or breakdown of control measures and to an increasing resistance of the vector to insecticides and falciparum malaria to chemotherapy. Thus there is an urgent need to develop a vaccine effective against malaria.

Most attempts to develop a vaccine have focused on trying to identify single proteins that are capable of inducing protective immune responses in the host against the relevant species and stage of parasite. This is in itself an enormous task because of the complexity of the parasite's life cycle, the number and diversity of antigens within the spectrum of polypeptides synthesised, and the superficial understanding we have of the important aspects of the immune system that control malaria. Nevertheless, several proteins have been identified by using monoclonal antibodies, sera from immune individuals and antibodies to fragments of genes expressed from libraries in bacteria. Using a variety of criteria, including the effects of antibodies in vitro or in vivo on the parasite's growth and development, direct immunization studies, and subcellular location or possible function of the protein, several vaccine candidates have been proposed.

One such candidate is the Merozoite Surface Protein-1 (abbreviated to MSP1, but also known as MSA1, PMMSA, P.190 or gP195) located on the exterior of the merozoite, the parasite stage which invades erythrocytes. MSP1 is found on the merozoite surface of all malaria parasite species and is therefore an ideal target for a candidate malaria vaccine. The precursor protein is, in fact, proteolytically processed to form a complex of several polypeptides of differing molecular weights (Holder et al., [1987] Parasitology 94, 199–208).

It has been shown that the protein purified from *P. falciparum* will protect against blood stage challenge (Siddiqui et al., [1987] Proc. Natl. Acad. Sci. 84, 3014–3018). Two different reports have shown that monoclonal antibodies to this molecule will inhibit invasion in vitro (Pirson & Perkins, [1985] Journal of Immunology 134, 1946–1951; Blackman et al., [1990] Journal of Experimental Medicine 172, 379–382). In this second study the target of the antibodies was identified as a 19 kDa fragment derived from the C-terminus of the precursor and which is retained on the merozoite surface during invasion of erythrocytes. A monoclonal antibody specific for the homologous protein expressed by *P. yoelii* inhibits growth of this parasite

2 in vivo after passive transfer to infected mice (Majarian et al. Journal of Immunology 132, 3131–3137 [1984], and the epitope has been mapped to the C-terminal sequence of this protein (Burns et al., [1989] Journal of Immunology 143, 2670–2676).

Antibodies to the C-terminal region of the precursor do not bind to the protein after it has been treated with reducing agents such as mercaptoethanol or dithiothreitol, suggesting that the numerous cysteine residues in this area are involved in specific disulphide bonding. Since it is a well known observation that proteins expressed as intracellular proteins in *E. coli* do not form correct disulphides, expression and secretion using the baculovirus/insect cell system has been used for the terminal 293 amino acids of the precursor (Murphy et al., [1990] Parasitology 100, 177–183).

In the further development of these polypeptides towards a practical product, their isolation from the parasite is not a feasible proposition, therefore much current research is devoted to using recombinant DNA or peptide synthesis techniques to get round this problem. However, the expression of a gene sequence in bacteria is not always straightforward because the antigenic properties of the product may not be the same as the native protein due to incorrect folding and assembly of the polypeptide during synthesis. Thus precise mapping of the protective monoclonal antibodies beyond reaction with a 56 kDa species (Pirson & Perkins, 1985) or the 19 kDa species (Blackman et al., [1990] Journal of Experimental Medicine 172, 379–382), which corresponds to the C-terminal 114 amino acids (Blackman et al., [1991] Molecular and Biochemical Parasitology 49, 29–34) has not been reported, nor has the effective expression of the target in *E. coli*.

The present invention is based on the surprising discovery that it is possible to define the target of protective antibodies directed against a merozoite surface protein as a short stretch of amino acids, and that this target can be synthesised in bacteria in a form indistinguishable from that in the native protein.

SUMMARY OF THE INVENTION

Figure 1A:
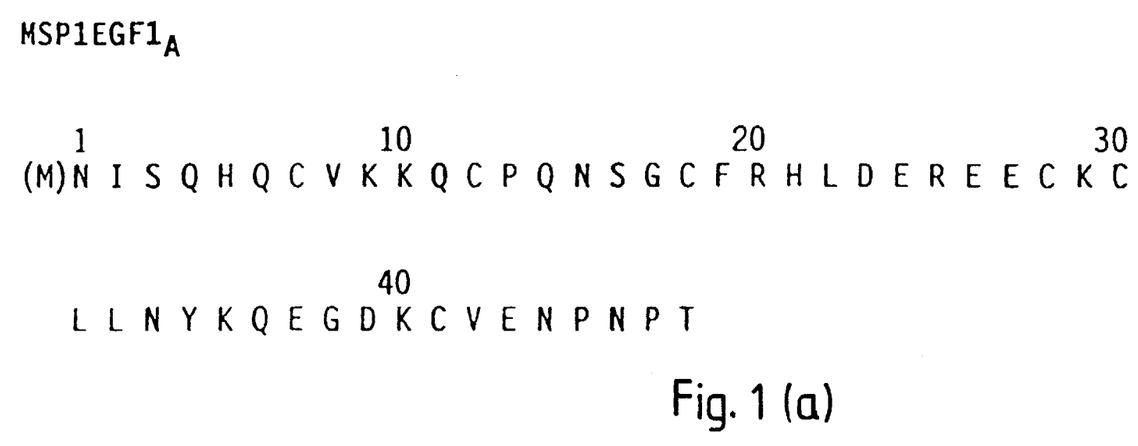
FIGS. 1a and b show the sequences of two allelic variants of the EGF1-like domain, FIGS. 2a and b show the sequences of two allelic variants of the EGF2-like domain.

In one aspect the invention provides a polypeptide comprising the sequence substantially as shown in FIG. 1a (Seq. ID No.1 in the attached sequence listing), or functional equivalents thereof, in isolation from sequences naturally occurring adjacent thereto in the MSP 1 protein.

Figure 2A:
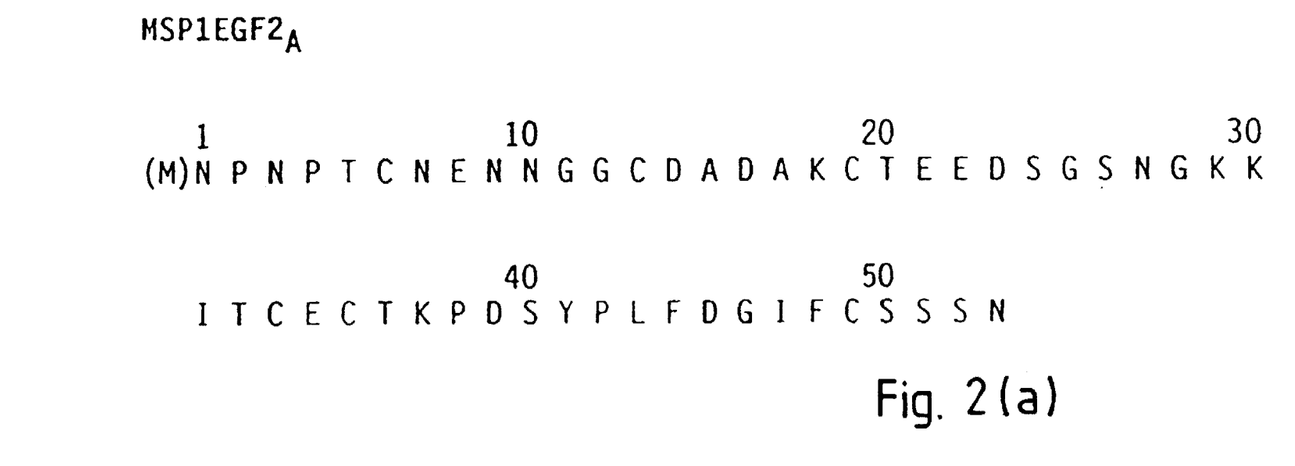

In another aspect the invention provides a polypeptide comprising the sequence substantially as shown in FIG. 2a (Seq. ID No.3), or functional equivalents thereof, in isolation from sequences naturally occurring adjacent thereto in the MSP 1 protein.

FIG. 1 shows the amino acid sequence of two allelic variants (A and B, Seq. ID Nos. 1 and 2 respectively) of the polypeptide known as the EGF1-like domain. FIG. 2 shows the amino acid sequence of two allelic variants (A and B, Seq. ID Nos. 3 and 4 respectively) of the sequence of the polypeptide known as the EGF2-like domain. It is clear to those skilled in the art that other minor alterations can be made to the sequence of EGF1-like or EGF2-like without significantly altering the biological properties thereof, so as to result in a functional equivalent.

For example, as well as allelic variants, functional equivalents might include those in which there are one or more conserved amino acid substitutions (i.e. the substitution of an amino acid for one with similar properties). Other substitutions which could be made are those which change an amino acid from the MSP1 sequence to that from the Epidermal Growth Factor sequence, which substantially preserve the EFG-like structure. Alternatively, or in addition, minor additions, deletions or truncations of the MSP1 EGF-like sequences could be made. Other obvious functional equivalents are those EGF-like domains present in the MSP protein of other species of Plasmodium (such as the four species known to infect humans, or the mouse pathogen *P. yoelii*).

It should be stated that the N-terminal methionine residues shown in the sequence of the EGF1-like (FIG. 1) and EGF2-like (FIG. 2) domains are not essential. They are optional features which allow for cleavage of the EGF-like domains from any associated amino acid sequence by treatment with cyanogen bromide (CNBr).

The sequence of the gene encoding MSP1 has been determined for 2 strains of *P. falciparum*: Wellcome/T9/94 and MAD20 (Blackman et al., (1991) Molecular and Biochemical Parasitology 49, 29–34 and Tanabe et al., [1987] Journal of Molecular Biology 195, 273–287, respectively). The inventors were able, by means of PCR, to obtain stretches of DNA encoding two epidermal growth factor (EGF)-like domains, (EGF1-like and EGF2-like) which have been identified in these genes (Blackman et al., [1991] ibid.).

The sequences encoding the EGF1-like and EGF2-like domains were inserted into plasmids. The resulting plasmid constructs were able to direct the expression of the EGF-like domains as fusion proteins with glutathione S-transferase. Thus in another aspect the invention provides a vector comprising the sequence encoding EGF1-like and/or EGF2-like domain in isolation from sequences naturally occurring adjacent thereto in the MSP1 protein.

Generally the vector defined above is capable of expressing the EGF1-like and/or EGF2-like sequences.

They may be expressed in such a way the the EGF-like sequences retain the conformation which they adopt in the MSP1 protein.

In another aspect the invention provides a method of producing the EFG1-like domain and/or the EGF2-like domain, in isolation from other MSP1 sequences, in the conformation they adopt in MSP1, comprising inserting the vector defined above capable of expressing the EGF1-like and/or the EGF2-like domain in a suitable host cell, growing the host cell and isolating the EGF1-like and/or EGF2-like domain so produced.

In a further aspect the invention provides a nucleotide sequence comprising the sequence encoding the EGF1-like domain and/or the EGF2-like domain or functional equivalents thereof in isolation from other MSP1-encoding nucleotide sequences. Such functional equivalents include those sequences which whilst possessing a different nucleotide sequence, by virtue of the degeneracy of the genetic code, encode the same amino acid sequence (or an amino acid sequence containing conserved substitutions or minor deletions, additions or truncations) and those nucleotide sequences which hybridise to the complement of the nucleotide sequence of the invention.

Typically, the EGF-like domains are expressed as fusion proteins.

Preferably the fusion protein should be one which allows for ease of purification such as fusion with glutathione S-transferase, as described in the Examples. Other such readily-purified fusion proteins are known to those skilled in the art.

In the embodiment described in Example 1, the fusion protein is such that the EGF-like domains may be cleaved from the non-MSP1 polypeptide sequence.

In a further aspect the invention provides a host cell transformed with the vector defined above. The transformed host cell may be of bacterial, plant, fungal or animal origin.

Expression of the EGF-like domains in their native conformation, as described in Example 1, (as judged by their reaction with antibodies which are known to inhibit malaria parasite replication in vitro), may allow for the use of recombinant DNA-derived material as a vaccine to induce a protective immune response against malaria, which is supported by the data presented in Examples 2 and 3.

Thus in another aspect the invention provides a vaccine comprising the sequence shown in FIG. 1 or FIG. 2 or functional equivalents thereof. Preferably the vaccine comprises the sequence of both EGF-like domains or functional equivalents thereof. Conveniently the vaccine comprises the polypeptide in its native conformation and is generally administered with an appropriate adjuvant (e.g. alum). Typically the EGF-like domains will be carried in a physiologically acceptable carrier and/or be fused to another immunogen.

In another aspect the invention provides a method of treating a human body by administering a vaccine comprising the sequences shown in FIG. 1 or FIG. 2 or functional equivalents thereof.

BRIEF DESCRIPTION OF THE DRAWINGS

The invention may be better understood by reference to the Examples and the following drawings in which.

EXAMPLE 1

Oligonucleotides derived from the sequence of T9/94 were used to act as primers for a polymerase chain reaction. The sequences of these primers are shown below:

EGF1 5' primer (Seq. ID No. 5 in the attached sequence listing):

EGF1 5' primer (Seq. ID No. 5 in the attached sequence listing):
5' TAAGAGCTCGGGATCCAGATGAACATTTCACAACACCAATGC 3'

EGF1 3' primer (Seq. ID No. 6):
5' TCCGAGCTCAGATCTTAAGTAGGATTTGGATTTTC 3'

EGF2 5' primer (Seq. ID No. 7):
5' TAAGAGCTCGGGATCCAGATGAATCCAAATCCTACTTGTAAC 3'

EGF2 3' primer (Seq. ID No. 8):
5' TCCGAGCTCAGATCTTAGTTAGAGGAACTGCAGAA 3'

At the 5' end of the 5' primers is an extension to introduce restriction sites for SacI and BamHI, followed by an ATG methionine (Met) codon. The significance of this Met codon is discussed below. Immediately 3' of the Met codon is a sequence of 21 bases, complementary to the start of either of the EGF1-like sequence (859–879) or the start of the EGF2-like sequence (988–1008). Each 3' primer contains, in the 5'-3' direction, an extension to introduce restriction sites for SacI and Bgl II, and a TAA stop codon followed by a sequence of 18 bases complementary to either the 3' end of the EGF1-like sequence (985–1002) or the 3' end of the EGF2-like sequence (1129–1146).

The PCR products were cut with BamHI and BglII and inserted into BamHI-restricted pGex-3x (Smith & Johnson, [1988], Gene 67, 31–40). The ligation reaction products were used to transform *E. coli* strain DH5alpha. Recombinants with the insert in the correct orientation were identified by restriction enzyme analysis. The junctions of the new constructs were confirmed by DNA sequencing.

Figure 1B:
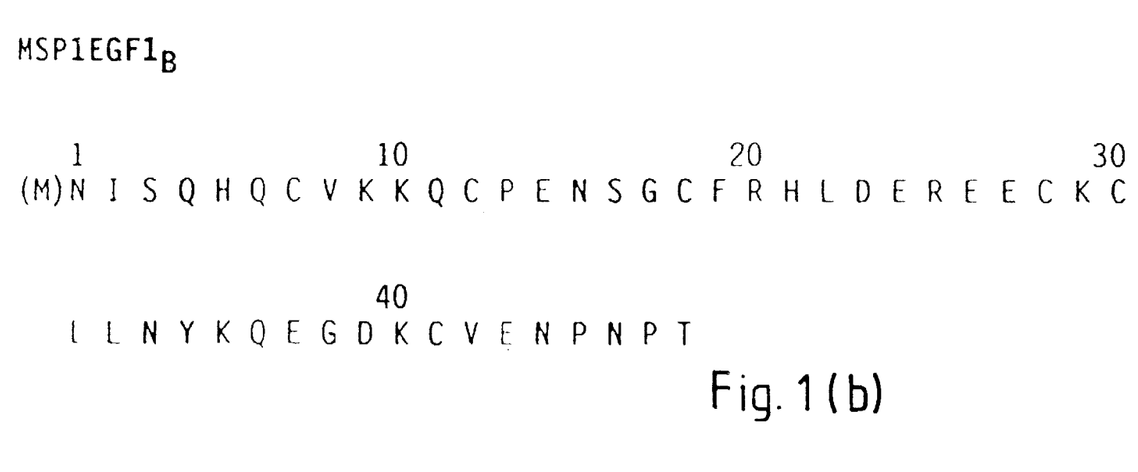

FIGS. 1A and 1B show the amino acid sequence of the region amplified as the first EGF-like domain for the two allelic types, MSP1EGF1$_A$ (eg. Wellcome, T9/94 strains) and MSP1EGF1$_B$ (eg. MAD20 strain). The amino terminal methionine was an optional feature introduced to facilitate cleavage from the recombinant protein.

Figure 2B:
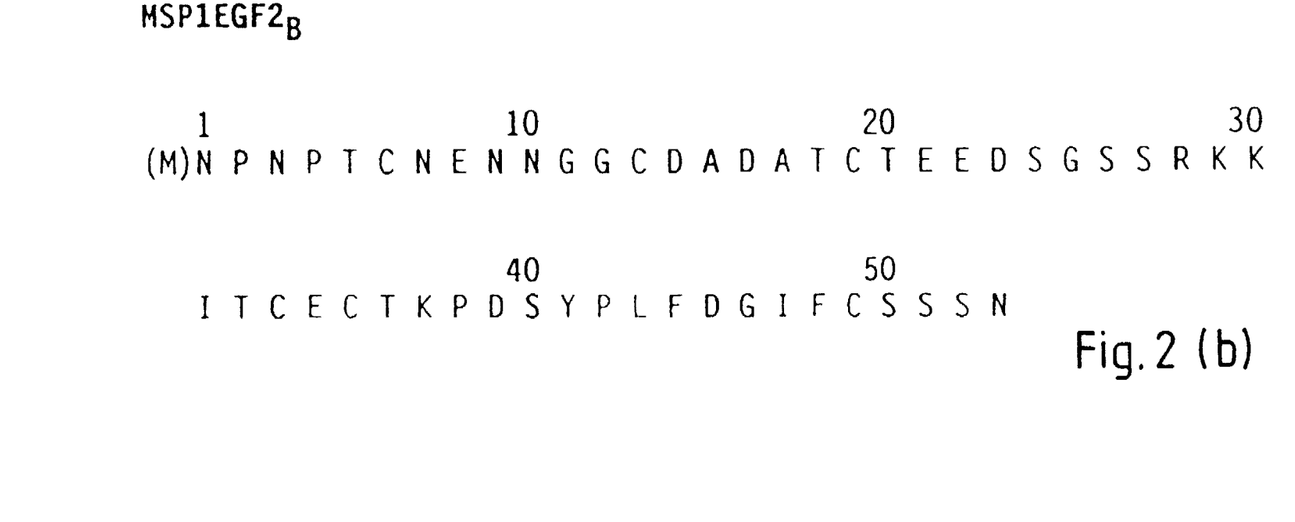

FIGS. 2A and 2B show the amino acid sequence of the region amplified as the second EGF-like domain for the two allelic types, MSP1EGF2$_A$ (eg. Wellcome, T9/94 strains) and MSP1EGF2$_B$ (eg. MAD20 strain). The amino terminal methionine was an optional feature introduced to facilitate cleavage from the recombinant protein.

Figure 3:
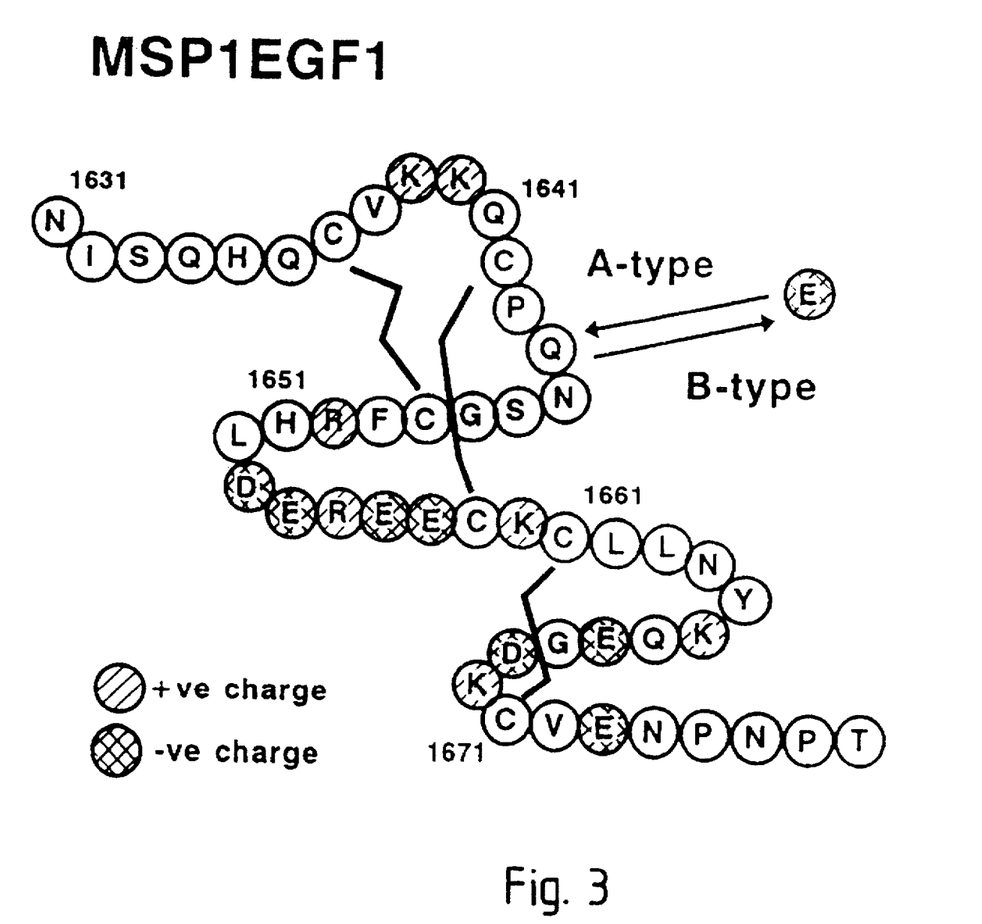
FIG. 3 shows the predicted structure of MSP1 EGF, based on the structure of human EGF (SEQ ID NO:12)

FIG. 3 shows amino acids 1631–1678 of *P. falciparum* MSP1 EGF1-like domain, modelled on the solution structure of human EGF. In EGF, cysteines are paired in disulphides (shown in FIG. 3 as solid lines): $C_1$ to $C_3$; $C_2$ to $C_4$ and $C_5$ to $C_6$. The net charge, at neutral pH, is shown for each amino acid as either positive, negative or no net charge. In *P. falciparum* MSP1EGF1, only one amino acid varies between strains; either Q1644 (with no net charge) in A-type strains or E1644 (with net negative charge) in B-type strains.

For expression studies recombinant bacteria were grown overnight at 37° C. in L-broth. The cultures were then diluted 5-fold with fresh medium and IPTG was added to a final concentration of 0.25 mM. After a further 3 hours growth, cells were harvested. Cell pellets were resuspended in 25 mM Tris-HCl, 1 mM EDTA, pH8.0 containing 0.2% (V/V) nonidet P40, and PMSF in isopropanol was added to a final concentration of 1 mM. 1 mg per ml of lysozyme was added and the sample was left on ice for 2 hours, then MgSO$_4$ to 2 mM and DNAse to 20 mg per ml were added and the mixture left for a further 2 hours. The lysate was centrifuged at 17,000 g for 20 minutes at 4° C. Soluble GST fusion proteins were purified from the supernatant by chromatography on glutathione-agarose (obtained from Sigma Chemical Company, catalogue number G9761) and eluted with 8M urea. Insoluble proteins in the pellet fraction were washed twice with 50 mM Tris-HCl, 5 mM EDTA, 5 mM EGTA, 1 mM PMSF pH8.0 containing first 1% (V/V) NP-40 and then 0.5M KSCN, and resuspended in 25 mM Tris-HCl, 1 mM EDTA pH8.0. To biosynthetically label the proteins, the recombinants were grown as described above and synthesis induced in the presence of $^{35}$S cysteine in minimal medium.

The design of the PCR oligonucleotide primers, (to introduce a Met residue at the start of the EGF-like domains), allowed the MSP1 sequences to be cleaved from the fusion protein by the use of Cyanogen bromide (CNBr), which cleaves polypeptide chains at Met residues.

Figure 4:
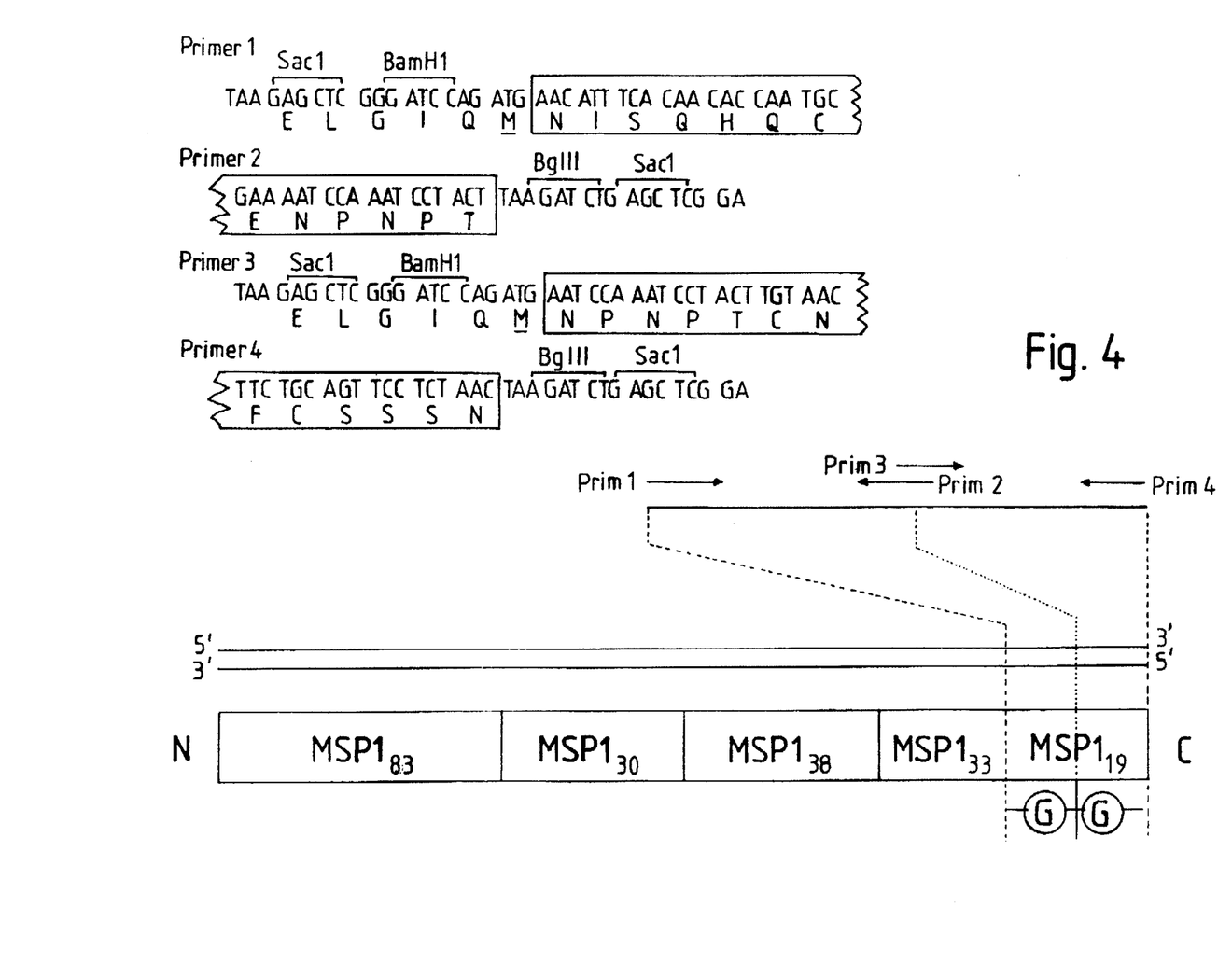
FIG. 4 shows the sequence of the oligonucleotide primers (SEQ ID NO:5 through SEQ ID NO:8 and SEQ ID NO:13 through SEQ ID NO:16) used to amplify the EGF1-like and EGF2-like coding sequences and their location relative to the MSP1 protein.

FIG. 4 shows the oligonucleotide primers used for amplification of MSP1EGF1 (1 and 2) and MSP1EGF2 (3 and 4), containing the appropriate restriction enzyme cleavage sites and the methionine codons. In the case of Primers 2 and 4 the reverse complement sequence is shown. In the second half of this figure is presented a schematic diagram of MSP1 showing the positions of the natural fragments derived by processing of this precursor, the positions of the EGF-like domains and the location of the oligonucleotide primers used to amplify them.

The hybrid protein was dissolved at 5 mgs per ml in 70% (v/v) formic acid and treated with cyanogen bromide (1000-fold molar excess, 3.3 mg CNBr/mg protein) at ambient temperature for 24 hours in the dark. After 5-fold dilution with water, excess reagents were removed by lyophilisation or by dialysis against 0.1M ammonium acetate, pH 5.0 without prior dilution using a Spectrapore 7 dialysis membrane.

To purify further the first EGF domain, the CNBr digest was dissolved in 0.1M ammonium acetate, pH5.0 and applied to an affinity column of monoclonal antibody 111.4 (Holder et al., [1985] Nature 317, 270–273), coupled to Sepharose and equilibrated with this buffer. After washing, the bound material was eluted with 0.1M glycine adjusted to pH 2.5 with HCl.

It was found that expression of the EGF-like domains in this manner allowed them to adopt a native conformation, as judged by their reaction with antibodies described below.

Figure 5:
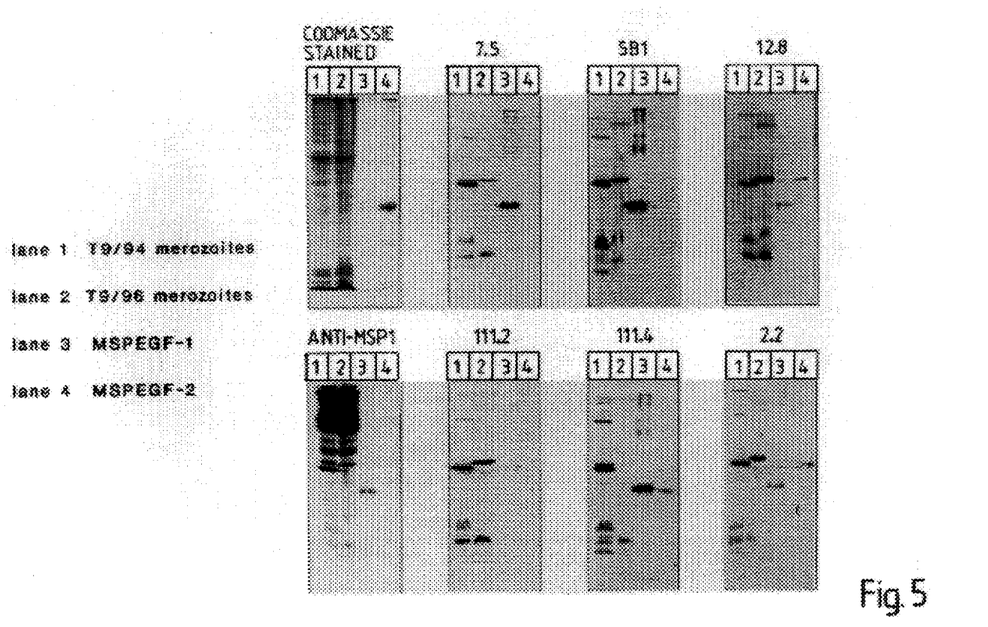
FIG. 5 shows the results of immunoblot ("Western" blot) analysis of merozoite extracts and EGF-like domain-containing fusion proteins.

Proteins were analysed by polyacrylamide gel eletrophoresis in the presence of sodium dodecyl sulphate (SDS-PAGE) or SDS and urea (Swank & Munkres, 1971). After transfer of proteins to nitrocellulose, antibody binding was detected using alkaline phosphatase-conjugated second antibody and a chromogenic substrate. The results are shown in FIG. 5. Radiolabelled proteins in immunoprecipitates formed with the specific antibodies were also analysed on polyacrylamide gels.

FIG. 5 shows the reaction of a variety of antibody preparations with proteins on a Western blot. The proteins were either extracts of merozoites (lane 1, from clone T9/94; lane 2, from clone T9/96) or the purified GST fusion protein with MSP1EGF1$_A$ (lane 3) and MSP1EGF2$_A$ (lane 4). After separation by electrophoresis in the presence of SDS and the proteins were either stained with Coomassie blue or transferred to nitrocellulose and probed with polyclonal (anti-MSP1) or monoclonal antibodies.

Proteins were also subjected to chromatography on a HPLC system, using a Vydax C4 column, eluted with 0.1% trifluoroacetic acid and acetonitrile over a 0% to 100% gradient of acetonitrile.

These experiments showed that the EGF-like domains are in their native conformation, reacting with antibodies which are known to inhibit malaria parasite replication in vitro.

As already described, it is possible to isolate the EGF-like polypeptides from other portions of a fusion protein. However, it may be advantageous to keep the EGF-like domains coupled to other polypeptides or other substances, so as to enhance the protective immune response against malaria. For instance, the EGF-like domains could be coupled to other protective antigens or epitopes from the malaria parasite.

EXAMPLE 2

The successful expression of MSP1 EGF-like domains in their natural conformation prompted experiments to investigate the ability of the EGF-like domains to stimulate a protective immune response.

The mouse, which can be infected by *P. yoelii*, is the accepted model for human malaria and has been widely studied. Thus the first step was to clone the EGF-like domains from *P. yoelii* MSP1.

DNA coding for the combined EGF-like domains of *P. yoelii* MSP1 was synthesised by PCR amplification of *P. yoelii* genomic DNA using the primers shown below.

Primer PyMSPEGF1 5' primer (42 mer, Seq. ID No.9):

Primer PyMSPEGF1 5' primer (42 mer, Seq. ID No. 9):

```
     E   L   G   I   H   M   D   G   M   D   L   L   G
TAA GAG CTC GGG ATC CAC ATG GAT GGT ATG GAT TTA TTA GGT
    Sac 1       Bam H1
```

Primer PyMSPEGF4 3' primer (Seq. ID No. 10)
TC CGA GCT CAG ATC TTA GCT GGA AGA ACT ACA GAA

```
 F   C   S   S   S   S  *(STOP)
(TTC TGT AGT TCT TCC AGC TAA GAT CTG AGC TCG GA)
                            Bgl II    Sac 1
```

Figure 6:
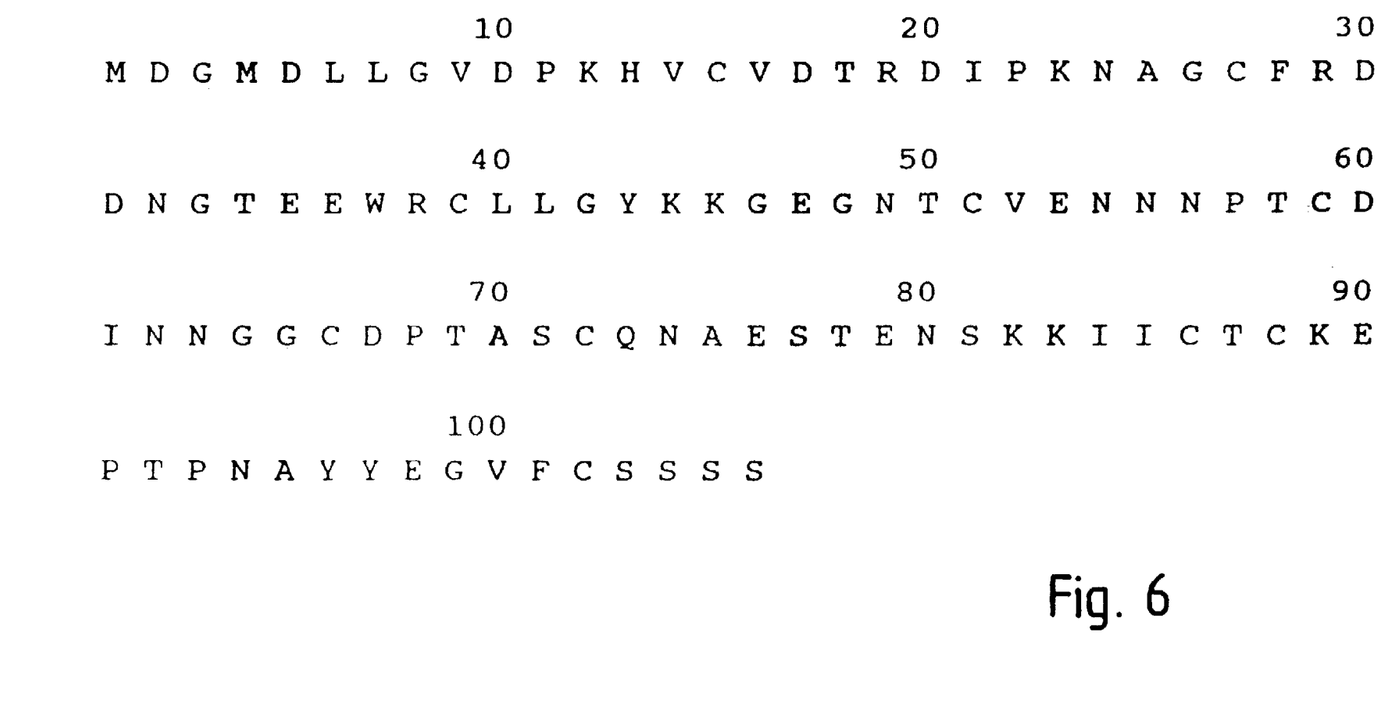
FIG. 6 shows the amino acid sequence (Seq. ID No. 11) of the combined EGF-like domains from *P. yoelii*.

The amplification products were treated with the restriction enzymes BamH1 and Bgl11, purified and then ligated into the expression vector pGex3x. After transformation of *E. coli* DH5 alpha to ampicillin resistance, individual clones were screened by restriction enzyme digestion and analysis of protein production. A single clone expressing the appropriate fusion protein (i.e. the two EGF-like domains fused to the C terminus of glutathione S-transferase (GST)) was selected and the DNA sequence of the insert was confirmed by DNA sequencing. The amino acid sequence of the amplified region of *P. yoelii* MSP1, containing the combined EGF-like domains is shown in FIG. 6.

Bacterial cultures of the desired clone were grown overnight at 37° C. in L-broth and diluted 1:5 (v/v) to a final volume of 500 ml in fresh prewarmed medium and grown for a further hour before protein synthesis was induced by the addition of IPTG to 0.1 mM. Following a further 3 h incubation bacterial cells were harvested by centrifugation at 5,000 g for 10 min and the bacterial cells were frozen at −70° C. Control cultures were also grown which expressed the GST protein alone and cells from these cultures were also stored at −70° C.

GST and GST/EGF-like fusion proteins were purified from bacterial lysates by binding and elution from glutathione-agarose. Cell paste equivalent to 500 ml induced culture was resuspended on ice in 10 ml "cell lysis buffer" (25 mM Tris-HCl pH 8.0, 0.2% (v/v) Nonidet P40), 1 mM EDTA), containing 1 mM PMSF. Lysozyme was added to 1 mg ml$^{-1}$ and after 2 hrs on ice MgSO$_4$ and deoxyribonuclease (type I) were added to final concentrations of 2 mM and 20 ug ml$^{-1}$ respectively. After a further 2 hrs on ice the cell lysate was centrifuged at 39,000 g for 20 minutes. The supernatant fraction was passed over a chromatography column containing 50 ml glutathione-agarose and then the column was washed extensively with phosphate-buffered saline (PBS). GST or GST-fusion protein were eluted from the column using 8M urea in 50 mM Tris pH 7.5. Eluted fractions containing fusion protein were identified by SDS PAGE with Coomassie blue staining. Peak fractions were pooled and dialysed extensively againt PBS. The purity of the protein was confirmed by gel electrophoretic analysis and amino acid analysis.

As well as immunising mice with GST (control group) and GST-fusion protein (experimental group), it was decided to prepare combined MSPEGF-like domains in isolation from GST and immunise a third group of mice with this preparation. To prepare the inoculum, bacterial lysates containing the GST-EGF fusion were passed through a column of glutathione-agarose as described above. The column running buffer was exchanged for factor Xa digestion buffer (50 mM Tris-HCl pH8.0, 100 mm NaCl, 1 mM CaCl$_2$). Buffer containing factor Xa (25 ug protein) was loaded and then the column was left to stand for 8 hours at 4° C. The released combined domain protein was eluted and then the process was repeated. Fractions were analysed using polyacrylamide gel electrophoresis in the presence of SDS and then pooled.

After dialysis against 50 mM ammonium bicarbonate the samples were lyophilised, and redissolved in PBS. The purity of the protein was confirmed by gel electrophoresis, amino acid analysis and sequence analysis. The N-terminal amino acid sequence of the cleaved fragment was determined and found to be: G I H M D G M D L L G (Seq. ID No. 11). This agrees with that from the predicted cleavage site of factor Xa and the deduced amino acid sequence from the cloned DNA at the start of the combined EGF-like domains.

In a first set of immunisation/challenge experiments, the purified proteins were used to immunise groups of mice, which were subsequently challenged with 5000 parasite-infected red blood cells from a donor mouse, according to the schedule shown below.

| Immunisation | Day | Amount of protein (in micrograms) | Adjuvant |
|---|---|---|---|
| Primary | 0 | 10 | Freund's complete |
| First boost | 21 | 40 | Freund's incomplete |
| Second boost | 43 | 40 | Freund's incomplete |
| Challenge | 57 | | |

Group 1 was immunised with combined EGF-like domains cleaved from GST, group 2 was immunised with the intact fusion protein (GST-combined EGF-like domains), whilst group 3 received the GST carrier protein alone. At day 54 a serum sample was taken from each mouse to measure the antibody levels by indirect immunofluorescence assay (IFA) against the blood stage parasite.

The results are shown in Table 1 which, for each group, shows the development of infection (% parasitaemia) in individual immunised mice at different times (days) after challenge. Development of parasitaemia was monitored regularly in smears of blood stained with Giemsa's stain and the percentage of infected red cells were calculated. The absence of parasitaemia was defined as no detectable parasites in 50 microscopic fields (each containing 200 erythrocytes).

In this experiment, all the mice in groups 1 and 2 had an IFA titre of greater than 1/5120.

Table 1 shows that eleven of twelve mice immunised with the combined EGF-like domains, either free or attached to GST (Groups 1 and 2), showed no detectable parasites and that one animal experienced a merely transient parasitaemia. In contrast, all the animals in the control group immunised with GST alone (Group 3) developed a heavy parasitaemia and all but one died from an overwhelming infection during the period of the experiment. This result demonstrates the remarkably effective protection obtained by vaccination with the EGF-like domains either alone or attached to GST as a carrier protein.

EXAMPLE 3

A further experiment was conducted to confirm the results of the first experiment and to assess the importance of secondary structure in the immunising protein.

To disrupt the secondary structure of the fusion protein and prevent it from reforming, a sample was reduced with dithiothreitol and then alkylated with an excess of iodoacetamide. This treatment breaks the disulphide bonds in the protein and modifies the sulphydryl group of the cysteine residues by addition of a carboxyamidomethyl group. The fusion protein (1.2 mg) was dissolved in PBS containing 8M urea and 0.2M dithiothreitol, and incubated at 37° C. for 30 minutes to reduce all sulphydryl groups. An excess of iodoacetamide (360 ul of a 1M solution in 0.1M NaOH) was added and the incubation was allowed to continue for a further 30 minutes, periodically adding 10M NaOH to maintain the pH above 7. Finally the sample was dialysed extensively against PBS.

Thus, in a second set of challenge experiments mice were immunised with: the cleaved combined EGF-like domains (Group 1), the intact fusion protein (GST-combined EGF-like domains) (Group 2), the reduced and carboxyamidomethylated fusion protein (Group 3), the GST carrier alone (Group 4) and PBS (Group 5). The immunisation schedule was identical to that in the first experiment except that the second boost was given on day 42.

The experiment was performed in the same manner as the first except that absence of parasitaemia in the second experiment was defined as no detectable parasites in 40 microscopic fields (each containing 300 erythrocytes). The results are shown in Table 2.

By IFA analysis the sera of the mice in Group 1 had an antibody titre of greater than 1/5120 and those in Group 2 had a titre in excess of 1/10,240. Modification of the immunogen reduced the level of antibodies produced that reacted with the native protein: mice in Group 3 had serum antibody titres of 1/1280 to 1/5120. As shown in Table 2, after challenge on this occasion, 14 of 19 mice in the first two groups showed no detectable parasites, a further 4 mice experienced transient low level parasitaemia and one of the animals was not protected. In the control groups, all the mice immunised with PBS and adjuvant alone were fully susceptible and 8 of 10 mice immunised with GST alone were also not protected. Interestingly, reduction and alkylation of the protein used for the vaccination (Group 3) reduced the protection afforded to the mice. In this group all the mice became infected and 3 of 10 died, the remaining mice had a prolonged high parasitaemia. This result confirms the observed protection mediated by vaccination with the combined EGF-like domains and demonstrates the importance of epitopes constrained by the disulphide-bonds in mediating this protection.

TABLE 1

| | % PARASITAEMIA | | | | | | | | | | | |
|---|---|---|---|---|---|---|---|---|---|---|---|---|
| Day: | 3 | 4 | 6 | 8 | 10 | 11 | 12 | 13 | 14 | 15 | 16 | 17 |

1. Combined EGF-like domains, cleaved fragment.

| | | | | | | | | | | | | |
|---|---|---|---|---|---|---|---|---|---|---|---|---|
| 1 | 0 | 0 | 0 | 0 | 0 | 0 | 0 | 0 | 0 | 0 | 0 | 0 |
| 2 | 0 | 0 | 0 | 0 | 0 | 0 | 0 | 0 | 0 | 0 | 0 | 0 |
| 3 | 0 | 0 | 0 | 0 | 0 | 0 | 0 | 0 | 0 | 0 | 0 | 0 |
| 4 | 0 | 0 | 0 | 0 | 0 | 0 | 0 | 0 | 0 | 0 | 0 | 0 |
| 5 | 0 | 0 | 0 | 0 | 0 | 0 | 0 | 0 | 0 | 0 | 0 | 0 |
| 6 | 0 | 0 | 0.13 | 0.5 | 4.5 | 4 | 4 | 4.5 | 1 | 0.5 | 0.02 | 0 |
| Mean: | 0 | 0 | 0.021 | 0.083 | 0.75 | 0.667 | 0.667 | 0.75 | 0.167 | 0.083 | 0.003 | 0 |

2. Combined EGF-like domains attached to glutathione S-transferase.

| | | | | | | | | | | | | |
|---|---|---|---|---|---|---|---|---|---|---|---|---|
| 1 | 0 | 0 | 0 | 0 | 0 | 0 | 0 | 0 | 0 | 0 | 0 | 0 |
| 2 | 0 | 0 | 0 | 0 | 0 | 0 | 0 | 0 | 0 | 0 | 0 | 0 |
| 3 | 0 | 0 | 0 | 0 | 0 | 0 | 0 | 0 | 0 | 0 | 0 | 0 |
| 4 | 0 | 0 | 0 | 0 | 0 | 0 | 0 | 0 | 0 | 0 | 0 | 0 |
| 5 | 0 | 0 | 0 | 0 | 0 | 0 | 0 | 0 | 0 | 0 | 0 | 0 |
| 6 | 0 | 0 | 0 | 0 | 0 | 0 | 0 | 0 | 0 | 0 | 0 | 0 |
| Mean: | 0 | 0 | 0 | 0 | 0 | 0 | 0 | 0 | 0 | 0 | 0 | 0 |

3. Glutathione S-transferase alone.

| | | | | | | | | | | | | |
|---|---|---|---|---|---|---|---|---|---|---|---|---|
| 1 | 0.01 | 1.5 | 35 | 70 | D* | | | | | | | |
| 2 | 0.01 | 1.5 | 45.5 | D | | | | | | | | |
| 3 | 0.01 | 0.5 | 43 | 65 | D | | | | | | | |
| 4 | 0.02 | 1 | 53.5 | D | | | | | | | | |
| 5 | 0.02 | 0.2 | 9.5 | 35 | 35 | 35.5 | 49 | 51.5 | 26.5 | 70 | 46.5 | 44 |
| 6 | 0.02 | 0.5 | 37 | 41 | 26 | 28.5 | 43 | 20 | 10 | 9 | D | |
| Mean: | 0.015 | 0.866 | 37.25 | 52.75 | 30.5 | 32 | 46 | 35.75 | 18.25 | 39.5 | 46.5 | 44 |

*D, died.

TABLE 2

% PARASITAEMIA

| Day: | 3 | 4 | 5 | 6 | 7 | 8 | 9 | 10 | 11 | 12 | 13 | 14 | 15 | 16 | 17 | 18 | 19 | 20 | 21 | 22 |
|---|---|---|---|---|---|---|---|---|---|---|---|---|---|---|---|---|---|---|---|---|
| 1. Combined EGF-like domains, cleaved fragment. | | | | | | | | | | | | | | | | | | | | |
| 1 | | 0 | 0 | 0 | 0 | 0 | 0 | 0 | 0 | 0 | 0 | 0 | 0 | 0 | 0 | 0 | 0 | 0 | 0 | 0 |
| 2 | | 0 | 0 | 0 | 0 | 0 | 0 | 0 | 0 | 0 | 0 | 0 | 0 | 0 | 0 | 0 | 0 | 0 | 0 | 0 |
| 3 | | 0 | 0 | 0 | 0 | 0 | 0 | 0 | 0 | 0 | 0 | 0 | 0 | 0 | 0 | 0 | 0 | 0 | 0 | 0 |
| 4 | | 0 | 0 | 0 | 0 | 0 | 0 | 0 | 0 | 0 | 0 | 0 | 0 | 0 | 0 | 0 | 0 | 0 | 0 | 0 |
| 5 | | 0.04 | 8.1 | 17.5 | 15 | D | | | | | | | | | | | | | | |
| 6 | | 0 | 0 | 0 | 0 | 0 | 0 | 0 | 0 | 0 | 0 | 0 | 0 | 0 | 0 | 0 | 0 | 0 | 0 | 0 |
| 7 | | 0 | 0 | 0 | 0 | 0 | 0.008 | 0 | 0 | 0 | 0 | 0 | 0 | 0 | 0 | 0 | 0 | 0 | 0 | 0 |
| 8 | | 0 | 0 | 0 | 0 | 0 | 0 | 0 | 0 | 0 | 0 | 0 | 0 | 0 | 0 | 0 | 0 | 0 | 0 | 0 |
| 9 | | 0 | 0.02 | 0.3 | 1.6 | 0.26 | 2.9 | 2.9 | 0.13 | 0.008 | 0.008 | 0 | 0 | 0 | 0 | 0 | 0 | 0 | 0 | 0 |
| 10 | | 0 | 0 | 0 | 0 | 0 | 0.025 | 0.17 | 0.09 | 0.09 | 0.008 | 0 | 0 | 0 | 0 | 0 | 0 | 0 | 0 | 0 |
| Mean: | | 0.004 | 0.812 | 1.78 | 1.66 | 0.029 | 0.323 | 0.325 | 0.022 | 0.011 | 0.011 | 0.001 | 0 | 0 | 0 | 0 | 0 | 0 | 0 | 0 |
| 2. Combined EGF-like domains attached to glutathione S-transferase. | | | | | | | | | | | | | | | | | | | | |
| 1 | | 0 | 0 | 0 | 0 | 0 | 0 | 0 | 0 | 0 | 0 | 0 | 0 | 0 | 0 | 0 | 0 | 0 | 0 | 0 |
| 2 | | 0 | 0 | 0 | 0 | 0 | 0 | 0 | 0 | 0 | 0 | 0 | 0 | 0 | 0 | 0 | 0 | 0 | 0 | 0 |
| 3 | | 0 | 0 | 0 | 0 | 0 | 0 | 0 | 0 | 0 | 0 | 0 | 0 | 0 | 0 | 0 | 0 | 0 | 0 | 0 |
| 4 | | 0 | 0 | 0 | 0 | 0 | 0 | 0 | 0 | 0 | 0 | 0 | 0 | 0 | 0 | 0 | 0 | 0 | 0 | 0 |
| 5 | | 0 | 0 | 0 | 0 | 0 | 0 | 0 | 0 | 0 | 0 | 0 | 0 | 0 | 0 | 0 | 0 | 0 | 0 | 0 |
| 6 | | 0 | 0 | 0 | 0 | 0 | 0 | 0 | 0 | 0 | 0 | 0 | 0 | 0 | 0 | 0 | 0 | 0 | 0 | 0 |
| 7 | | 0 | 0 | 0 | 0 | 0 | 0 | 0 | 0 | 0 | 0 | 0 | 0 | 0 | 0 | 0 | 0 | 0 | 0 | 0 |
| 8 | | 0 | 0 | 0 | 0 | 0.017 | 0.008 | 0.033 | 0.058 | 0 | 0 | 0 | 0 | 0 | 0 | 0 | 0 | 0 | 0 | 0 |
| 9 | | 0 | 0 | 0 | 0 | 0 | 0 | 0 | 0 | 0 | 0 | 0 | 0 | 0 | 0 | 0 | 0 | 0 | 0 | 0 |
| Mean: | | 0 | 0 | 0 | 0 | 0.002 | 0.001 | 0.004 | 0.006 | 0 | 0 | 0 | 0 | 0 | 0 | 0 | 0 | 0 | 0 | 0 |
| 3. Combined EGF-like domains attached to glutathione S-transferase, reduced and carboxyamidomethylated. | | | | | | | | | | | | | | | | | | | | |
| 1 | | 0.21 | 10 | 30 | 42 | 20.5 | 31 | 49 | 54 | 52.5 | 52 | 46.5 | 47 | 53 | 45 | 33.5 | 18 | 0.5 | 0 | 0 |
| 2 | | 0 | 0.04 | 0.33 | 3.7 | 5.5 | 7.5 | 11 | 13.5 | 13 | 4.4 | 0.075 | 0 | 0 | 0 | 0 | 0 | 0 | 0 | 0 |
| 3 | | 0.04 | 0.79 | 12 | 13 | 12 | 15.5 | 31 | 25 | 52 | 56 | 49 | 46 | 33 | 19 | 13.5 | 2 | 0.008 | 0 | 0 |
| 4 | | 0.18 | 15.5 | 40 | 45 | 6 | 28 | 49.5 | 52 | 57 | 55.5 | 57 | 50 | 36 | 37.5 | | 18 | 0.08 | 0 | 0 |
| 5 | | 0.43 | 24 | 42.5 | 62 | D | | | | | | | | | | | | | | |
| 6 | | 0.07 | 9 | 31.5 | 26.5 | 21 | 31.5 | 47 | 49.5 | 50 | 61 | 65 | 49.5 | 50.5 | 62 | 54.5 | 54 | 60 | 56 | 45 |
| 7 | | 0.34 | 10 | 30.5 | 33 | 26.5 | 20 | 49 | 59 | 45 | 49.5 | 44 | 39.5 | 22.5 | 13 | 4.5 | 0.017 | 0 | 0 | 0 |
| 8 | | 0.11 | 7.5 | 23 | 34.5 | D | | | | | | | | | | | | | | |
| 9 | | 0.33 | 21 | 65 | D | | | | | | | | | | | | | | | |
| 10 | | 0.4 | 9 | 29 | 27.5 | 20 | 26 | 29 | 56 | 56 | 44.5 | 46 | 38 | 30 | 19.5 | 6.2 | 0.004 | 0 | 0 | 0 |
| Mean: | | 0.211 | 10.68 | 30.38 | 31.91 | 15.93 | 22.78 | 37.93 | 44.14 | 46.5 | 46.12 | 43.93 | 38.57 | 32.14 | 28 | 20.88 | 13.15 | 8.655 | 8 | 6.428 |
| 4. Glutathione S-transferase alone. | | | | | | | | | | | | | | | | | | | | |
| 1 | 0 | 1.9 | 19 | 47 | 61 | 43 | D | | | | | | | | | | | | | |
| 2 | 0.008 | 1.24 | 16 | 48 | 74.5 | D | | | | | | | | | | | | | | |
| 3 | 0 | 0.13 | 6.5 | 20 | 37 | 19.5 | 27 | 49 | 46.5 | 55 | 57.5 | 47 | 46 | 41 | 46 | 55.5 | 48 | 46.5 | 31 | 10.6 |
| 4 | 0 | 0.88 | 31 | 73.5 | D | | | | | | | | | | | | | | | |
| 5 | 0.008 | 0.32 | 20 | 61 | 84.5 | D | | | | | | | | | | | | | | |
| 6 | 0 | 1.03 | 25 | 70.5 | 69 | D | | | | | | | | | | | | | | |
| 7 | 0 | 0.94 | 26 | 54 | 77 | D | | | | | | | | | | | | | | |
| 8 | 0.008 | 3.4 | 25 | 63 | 78 | D | | | | | | | | | | | | | | |
| 9 | 0 | 0.13 | 6 | 23 | 36 | 17.5 | 3.3 | 15 | 20 | 18 | 25 | 21 | 9 | 0.09 | 0.017 | 0 | 0 | 0 | 0 | 0 |
| 10 | 0 | 0.19 | 15.5 | 44 | 66 | 51.5 | D | | | | | | | | | | | | | |
| Mean: | 0.002 | 1.016 | 19 | 50.4 | 64.78 | 32.87 | 15.15 | 32 | 33.25 | 363.5 | 41.25 | 34 | 27.5 | 20.54 | 23.0 | 27.75 | 24 | 23.25 | 15.5 | 5.3 |
| 5. Phosphate-buffered saline alone. | | | | | | | | | | | | | | | | | | | | |

| Day: | 3 | 4 | 5 | 6 | 7 | 8 | 9 | 10 | 11 | 12 | 13 |
|---|---|---|---|---|---|---|---|---|---|---|---|
| 1 | 0 | 0.23 | 13 | 51 | 68.5 | D | | | | | |
| 2 | 0.016 | 0.24 | 14.5 | 50 | 74 | D | | | | | |
| 3 | 0 | 0.07 | 7 | 38.5 | 75.5 | D | | | | | |
| 4 | 0 | 0.17 | 9.5 | 31.5 | 63 | 31 | 17.4 | 13 | 13.3 | D | |
| 5 | 0.016 | 0.52 | 17 | 71.5 | 79 | D | | | | | |
| Mean: | 0.006 | 0.25 | 12.2 | 48.5 | 72 | 31 | 17.4 | 13 | 13.3 | | |

*D, died.

We claim:

1. An isolated polypeptide comprising a sequence as shown in either of FIGS. 1(a) (SEQ. ID NO:1) or 1(b) (SEQ. ID NO:2) or the corresponding portion of MSP1 from a strain of *Plasmodium falciparum* other than Wellcome T9/94 and MAD20 in isolation from sequences naturally occurring adjacent thereto in the MSP-1 protein.

2. An isolated polypeptide comprising a sequence as shown in either of FIGS. 2(a) (SEQ. ID NO:3) or 2(b) (SEQ. ID NO:4) or the corresponding portion of MSP1 from a strain of *Plasmodium falciparum* other than Wellcome T9/94 and MAD20 in isolation from sequences naturally occurring adjacent thereto in the MSP-1 protein.

3. An isolated polypeptide comprising a sequence as shown in either of FIGS. 1(a) (SEQ. ID NO:1) or 1(b) (SEQ. ID NO:2) and a sequence as shown in either of FIGS. 2(a) (SEQ. ID NO:3) or 2(b) (SEQ. ID NO:4), or the corresponding portions of MSP1 from a strain of *Plasmodium falciparum* other than Wellcome T9/94 and MAD20 in isolation from sequences naturally occurring adjacent thereto in the MSP-1 protein.

4. An isolated nucleotide sequence encoding at least one polypeptide comprising a sequence as shown in any one of FIGS. 1(a) (SEQ. ID NO:1), 1(b) (SEQ. ID NO:2), 2(a) (SEQ. ID NO:3) or 2(b) (SEQ. ID NO:4), or the corresponding portion of MSP1 from a strain of *Plasmodium falciparum* other than Wellcome T9/94 and MAD20 in isolation from sequences naturally occurring adjacent thereto in the MSP-1 protein.

5. An isolated nucleotide sequence encoding a polypeptide comprising a sequence as shown in either of FIGS. 1(a) (SEQ. ID NO:1) or 1(b) (SEQ. ID NO:2) and a sequence as shown in either of FIGS. 2(a) (SEQ. ID NO:3) or 2(b) (SEQ. ID NO:4), or the corresponding portions of MSP1 from a strain of *Plasmodium falciparum* other than Wellcome T9/94 and MAD20 in isolation from sequences naturally occurring adjacent thereto in the MSP-1 protein.

6. A vector, comprising the nucleotide sequence of claim 4.

7. The vector according to claim 6, which when inserted into a suitable host cell allows for the expression of a polypeptide comprising of a sequence as shown in any one of FIGS. 1(a) (SEQ. ID NO:1), 1(b) (SEQ. ID NO:2), 2(a) (SEQ. ID NO:3) or 2(b) (SEQ. ID NO:4), or the corresponding portion of MSP1 from another strain of *Plasmodium falciparum* in isolation from sequences naturally occurring adjacent thereto in the MSP-1 protein.

8. The vector according to claim 7, wherein said polypeptide is expressed as a fusion protein.

9. The vector according to claim 8, wherein said fusion protein comprises a moiety which facilitates the purification of the expressed polypeptide.

10. The vector according to claim 8, wherein said fusion protein is such that said polypeptide may be cleaved from the rest of the protein.

11. A vector comprising the nucleotide sequence of claim 5.

12. The vector according to claim 11, which when inserted into a suitable host cell allows for the expression of a polypeptide comprising a sequence as shown in any one of FIGS. 1(a) (SEQ. ID NO:1) or 1(b) (SEQ. ID NO:2), and a sequence as shown in any one of FIGS. 2(a) (SEQ. ID NO:3) or 2(b) (SEQ. ID NO:4), or the corresponding portions of MSP1 from a strain of *Plasmodium falciparum* other than Wellcome T9/94 and MAD20 in isolation from sequences naturally occurring adjacent thereto in the MSP-1 protein.

13. The vector according to claim 12, wherein the polypeptide is expressed as a fusion protein.

14. The vector according to claim 13, wherein said fusion protein comprises a moiety which facilitates purification of the expressed polypeptide.

15. The vector according to claim 13, wherein said fusion protein is such that said polypeptide may be cleaved from the rest of the protein.

16. A method of making a polypeptide comprising a sequence as shown in any one of FIGS. 1(a) (SEQ. ID NO:1), 1(b) (SEQ. ID NO:2), 2(a) (SEQ. ID NO:3) or 2(b) (SEQ. ID NO:4) or the corresponding portion of MSP1 from a strain of *Plasmodium falciparum* other than Wellcome T9/94 and MAD20 in isolation from sequences naturally occurring adjacent thereto in the MSP-1 protein, said method comprising the steps of introducing the vector of any one of claims 6–15 into a suitable host cell; growing said host cell; and isolating the polypeptide so produced.

17. A host cell transformed with a vector according to any one of claims 6 to 15.

18. A vaccine suitable for use in the prevention and/or treatment of malaria due to *Plasmodium falciparum*, said vaccine consisting essentially of at least one polypeptide comprising a sequence as shown in any one of FIGS. 1(a) (SEQ. ID NO:1), 1(b) (SEQ. ID NO:2), 2(a) (SEQ. ID NO:3) or 2(b) (SEQ. ID NO:4) or the corresponding portion of MSP1 from strain of *Plasmodium falciparum* other than Wellcome T9/94 and MAD20 in isolation from sequences naturally occurring adjacent thereto in the MSP-1 protein, said vaccine further comprising a physiologically acceptable carrier.

19. A vaccine suitable for use in the prevention and/or treatment of malaria due to *Plasmodium falciparum*, said vaccine comprising a polypeptide consisting essentially of a sequence as shown in any one of FIGS. 1(a) (SEQ. ID NO:1) or 1(b) (SEQ. ID NO:2) and a sequence as shown in any one of FIGS. 2(a) (SEQ. ID NO:3) or 2(b) (SEQ. ID NO:4) or the corresponding portion of MSP1 from a strain of *Plasmodium falciparum* other than Wellcome T9/94 and MAD20 in isolation from sequences naturally occurring adjacent thereto in the MSP-1 protein, said vaccine further comprising a physiologically acceptable carrier.

20. The vaccine according to claim 18 or 19, wherein said polypeptide is present as a fusion protein.

21. A method of preventing and/or treating a human body for malaria due to *Plasmodium falciparum*, comprising administering an effective amount of a vaccine according to claim 18 or 19.

\* \* \* \* \*